(12) United States Patent
Smith et al.

(10) Patent No.: US 7,067,501 B2
(45) Date of Patent: Jun. 27, 2006

(54) ARYLOXYPHENYL AND ARYLSULFANYLPHENYL DERIVATIVES

(75) Inventors: Garrick P. Smith, Valby (DK); Gitte Mikkelsen, Ballerup (DK); Kim Andersen, Ridgewood, NJ (US); Daniel Greve, Stenlose (DK); Thomas Ruhland, Roskilde (DK); Stephen P. Wren, Hertfordshire (GB)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 10/851,769

(22) Filed: May 20, 2004

(65) Prior Publication Data

US 2005/0171061 A1     Aug. 4, 2005

Related U.S. Application Data

(63) Continuation of application No. PCT/DK02/00859, filed on Dec. 16, 2002.

(60) Provisional application No. 60/342,653, filed on Dec. 20, 2001.

(30) Foreign Application Priority Data

Dec. 20, 2001   (DK) ............................... 2001 01927

(51) Int. Cl.
*A61K 31/495* (2006.01)
*C07D 295/15* (2006.01)

(52) U.S. Cl. ............ 514/85; 514/255.03; 514/89; 514/277; 514/317; 544/231; 544/337; 544/394; 546/16; 546/22; 546/236; 546/237; 546/238; 546/341

(58) Field of Classification Search ............... 544/394, 544/337, 231; 514/255.03, 85
See application file for complete search history.

(56) References Cited

FOREIGN PATENT DOCUMENTS

| JP | 10-152470 A2 | 6/1998 |
| WO | WO 97/20533 | 6/1997 |
| WO | WO 98/17651 | 4/1998 |
| WO | 2005018676 | * 3/2005 |

OTHER PUBLICATIONS

Smith et al. Bioorganic & Medicinal Chemistry Letters, vol. 14, p. 4027-4030 (Aug. 2, 2004).*
Javitt et al., 1994, Amelioration of Negative Symptoms in Schizophrenia by Glycine, *Am. J. Psychiatry*, 151:1234-1236.
Kiritsy et al., 1978, Synthesis and Quantitative Structure-Activity Relationships of Some Antibacterial 3-Formylrifamycin SV N-(4-substituted phenyl)piperazinoacethydrazones *J. of Medicinal Chem.*, 21:1301-1307.
Leiderman et al., 1996, Preliminary Investigation of High-Dose Oral Glycine on Serum Levels and Negative Symptoms in Schizophrenia: An Open-Label Trial *Biol. Psychiatry*, 39:213-215.
Rison et al., 1995, Long-term Potentiation and N-Methyl-D-aspartate Receptors: Foundations of Memory and Neurologic Disease? *Neurosci. Biobehav. Rev.*, 19:533-552.
Truong et al., 1988, Glycine Involvement in DDT-Induced Myoclonus *Movement Disorders*, 3:77-87.
Yaksh, 1989, Behavioral and Autonomic Correlates of the Tactile Evoked Allodynia Produced by Spinal Glycine Inhibition: Effects of Modulatory Receptor Systems and Excitatory Amino Acid Antagonists *Pain*, 37:111-123.

* cited by examiner

*Primary Examiner*—Emily Bernhardt
(74) *Attorney, Agent, or Firm*—Darby & Darby

(57) ABSTRACT

The invention provides compounds of the formula

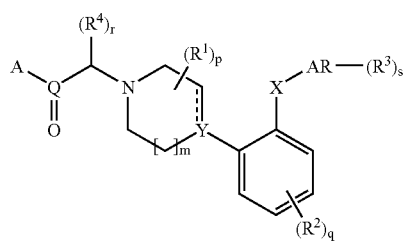

I wherein the substituents are as defined in the application. The compounds are valuable glycine transport inhibitors.

23 Claims, No Drawings

ARYLOXYPHENYL AND ARYLSULFANYLPHENYL DERIVATIVES

This application is a continuation of application no. PCT/DK02/00859, filed Dec. 16, 2002, and claims priority under 35 U.S.C. §119(e) of provisional application 60/342,653, filed Dec. 20, 2001. Each prior application is hereby incorporated by reference, in its entirety.

The present invention relates to novel compounds which are glycine transporter inhibitors and as such effective in the treatment of disorders in the CNS.

BACKGROUND OF THE INVENTION

Glutamic acid is the major excitatory amino acid in the mammalian central nervous system (CNS), and acts through two classes of receptors, the ionotropic and metabotrobic receptors, respectively. The ionotropic glutamate receptors are divided into three subtypes based on the affinities of agonists for these receptors, namely N-methyl-D-aspartate (NMDA), (R,S)-2-amino-3-(3-hydroxy-5-methylisoxazol-4-yl)propanoic acid (AMPA) and kainic acid (or kainate) receptors.

The NMDA receptor contains binding sites for modulatory compounds such as glycine and polyamines. Binding of glycine to its receptor enhances the NMDA receptor activation. Such NMDA receptor activation may, be a potential target for the treatment of schizophrenia and other diseases linked to NMDA receptor dysfunction. An activation can be achieved by an inhibitor of the glycine transporter.

Molecular cloning has revealed the existence of two types of glycine transporters, GlyT-1 and GlyT-2, wherein GlyT-1 can be further subdivided into GlyT-1a, GlyT-1b and GlyT-1c.

The NMDA receptor is blocked by compounds such as phencyclidine which induce a psychotic state which resembles schizophrenia. Likewise, the NMDA antagonists, such as ketamine, induce negative and cognitive symptoms similar to schizophrenia. This indicates that NMDA receptor dysfunction is involved in the pathophysiology of schizophrenia.

The NMDA receptor has been associated with a number of diseases, such as pain (Yaksh *Pain* 1989, 37, 111–123), spasticity, myuoclonus and epilepsy (Truong et. al. *Movement Disorders* 1988, 3, 77–87), learning and memory (Rison et. al. *Neurosci. Biobehav. Rev.* 1995, 19, 533–552).

Glycine transporter antagonists or inhibitors are believed to be highly beneficial in the treatment of schizophrenia (Javitt WO 97/20533).

Glycine transport antagonists or inhibitors could be useful for the treatment of both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke. Likewise, convulsive disorders such as epilepsy, spasticity or myoclonus may benefit from glycine transporter antagonists.

Clinical trials with glycine have been reported, Javitt et. al. *Am. J. Psychiatry* 1994, 151, 1234–1236 and Leiderman et. al. *Biol. Psychiatry* 1996, 39, 213–215. The treatment with high-dose glycine is reported to improve the symptoms of schizophrenia. There is a need for more efficient compounds for the treatment of NMDA associated diseases.

The present invention provides compounds which are potent inhibitors of the glycine transporter and consequently they are useful in treating diseases associated with NMDA dysfunction.

SUMMARY OF THE INVENTION

The present invention provides compounds of the general formula I

Y is N, C or CH;
X represent O or S;
m is 1 or 2;
p is 0, 1, 2, 3 or 4;
q is 0, 1 or 2;
s is 0, 1, 2 or 3;
r is 0, 1 or 2;
Q represents C, P—$OR^5$, or S=O, wherein $R^5$ represents hydrogen or $C_{1-6}$-alkyl;
A is $OR^6$ wherein $R^6$ represent hydrogen, $C_{1-6}$-alkyl, aryl or aryl-$C_{1-6}$-alkyl, wherein aryl may be substituted with halogen, $CF_3$, $OCF_3$, CN, $NO_2$ or $C_{1-6}$ alkyl;
AR represents phenyl or a heteraryl;
Each $R^4$ individually represents $C_{1-6}$-alkyl, $C_{3-8}$-cycloalkyl or $C_{3-8}$-cycloalkyl-$C_{1-6}$-alkyl;
The dotted line represents an optional bond;
Each $R^1$, which may be identical or different, is independently selected from the group consisting of $C_{1-6}$-alkyl, or two $R^1$, s attached to the same carbon atom may form a 3–6-membered spiro-attached cyclo-alkyl;
Each $R^2$, which may be identical or different, is independently selected from the groups consisting of halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl or —$NR^9R^{10}$ wherein $R^9$ and $R^{10}$ independently represent hydrogen, $C_{1-6}$-alk(en/yn)yl, $C_{3-8}$-cycloalk(en)yl, $C_{3-8}$-cycloalk(en)yl-$C_{1-6}$ alk(en/yn)yl or aryl, or $R^9$ and $R^{10}$ together form a 3–7-membered ring which optionally contains one further heteroatom;
Each $R^3$, which is substituted on AR, may be identical or different, is independently selected from a group consisting of halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)ylsulfonyl, aryl, aryl-$C_{1-6}$-alk(en/yn)yloxy, aryl-$C_{1-6}$-alk(en/yn)yl, $C_{1-6}$-alk(en/yn)yloxycarbonyl, acyl, —NHCO—$C_{1-6}$-alk(en/ yn)yl, —CONR$^{11}$R$^{12}$ wherein R$^{11}$ and R$^{12}$ independently represent hydrogen, C$_{1-6}$-alk(en/yn)yl, C$_{3-8}$-cycloalk(en)yl, C$_{3-8}$-cycloalk(en)yl-C$_{1-6}$-alk(en/yn)yl or aryl, or R$^{11}$ and R$^{12}$ together with the nitrogen to which they are attached form a 3–7-membered ring which optionally contains one further heteroatom;

or NR$^{13}$R$^{14}$ wherein R$^{13}$ and R$^{14}$ independently represent hydrogen, C$_{1-6}$-alk(en/yn)yl, C$_{3-8}$-cycloalk(en)yl, C$_{3-8}$-cycloalk(en)yl-C$_{1-6}$-alk(en/yn)yl or aryl; or R$^{13}$ and R$^{14}$ together with the nitrogen to which they are attached form a 3–7-membered ring which optionally contains one further heteroatom;

or two adjacent R$^3$ substituents together form a ring fused to the AR ring selected from the group consisting of

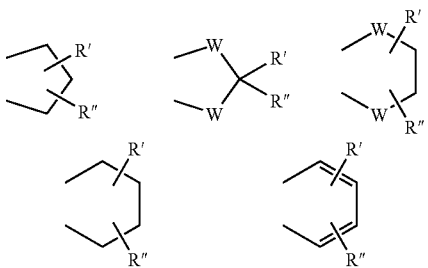

wherein W is O or S, and R' and R" are hydrogen or C$_{1-6}$-alkyl:

or two adjacent R$^3$ substituents together form a heteroaryl containing one or two heteroatom fused to the AR, or an acid addition salt thereof.

In case of the integers p, q, r or s being 0, the substituents are hydrogen.

If Y represents C, the dotted line is present. The dotted line is not present if Y represents N or CH.

The invention provides a compound of formula I as above for use as a medicament.

The invention provides a pharmaceutical composition comprising a compound of formula I as above or a pharmaceutically acceptable acid addition salt thereof and at least one pharmaceutically acceptable carrier or diluent.

The invention provides the use of a compound of formula I as above or a pharmaceutically acceptable acid addition salt thereof for the preparation of a medicament for the treatment of diseases selected from the group consisting of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus.

The invention provides a method for the treatment of diseases selected from the group consisting of schizophrenia, including both the positive and the negative symptoms of schizophrenia and other psychoses, and in the improvement of cognition in conditions where the cognitive processes are diminished, i.e. Alzheimer's disease, multi-infarct dementia, AIDS dementia, Huntington's disease, Parkinson's disease, amyotrophic lateral sclerosis or diseases wherein the brain is damaged by inner or outer influence, such as trauma to the head or stroke, and convulsive disorders such as epilepsy, spasticity or myoclonus in a living animal body, including a human, comprising administering a therapeutically effective amount of a compound of formula I as above or a pharmaceutically acceptable acid addition salt thereof.

DETAILED DESCRIPTION OF THE INVENTION

A preferred embodiment of the invention is wherein Y is N;

A preferred embodiment of the invention is wherein X is S;

A preferred embodiment of the invention is wherein Q is C;

A preferred embodiment of the invention is wherein A is OH;

A preferred embodiment of the invention is wherein p is 1 or 2.

A preferred embodiment of the invention is wherein m is 1;

A preferred embodiment of the invention is wherein q is 0.

A preferred embodiment of the invention is wherein r is 0 or 1;

A preferred embodiment of the invention is wherein s is 1 or 2.

A preferred embodiment of the invention is wherein AR is phenyl, thiophene, pyridyl, pyrimidyl, thiazolyl, imidazolyl or benzothizolyl;

A preferred embodiment of the above is wherein R$^4$ is CH$_3$;

A preferred embodiment of the invention is wherein AR is phenyl, r and q are both 0, p is 1 or 2, s is 1 or 2, r is 0 or 1; m is 1, R$^1$ is CH$_3$, A is OH, Q is C, Y is N and X is S;

An even more preferred embodiment of above is wherein each R$^3$ is independently selected from halogen, C$_{1-6}$-alkoxy or C$_{1-6}$-alkyl;

An even more preferred embodiment of the above is wherein R$^3$ is selected from the group consisting of Cl, F, OCH$_3$, t-butyl, 2-propyl or methyl;.

Particularly preferred embodiments of the invention are wherein the compound of the invention is any of the following:

(+/−)-{4-[2-(4-Methoxy-phenylsulfanyl)-phenyl]-trans-2,5-dimethyl-piperazin-1-yl}-acetic acid (+/−)-{4-[2-(4-Chloro-phenylsulfanyl)-phenyl]-trans-2,5-dimethyl-piperazin-1-yl}-acetic acid (+/−)-{4-[2-(4-tert-Butyl-phenylsulfanyl)-phenyl]-trans-2,5-dimethyl-piperazin-1-yl}-acetic acid (+/−)-{4-[2-(4-Fluoro-phenylsulfanyl)-phenyl]-trans-2,5-dimethyl-piperazin-1-yl}-acetic acid (+/−)-{4-[2-(4-tert-Butyl-phenylsulfanyl)-phenyl]-2-methyl-piperazin-1-yl}-acetic acid (+/−)-{4-[2-(4-iso-Propyl-phenylsulfanyl)-phenyl]-2-methyl-piperazin-1-yl}-acetic acid (+/−)-2-{4-[2-(4-tert-Butyl-phenylsulfanyl)-phenyl]-trans-2,5-dimethylpiperazin-1-yl}-propionic acid {4-[5-Chloro-2-(4-methoxy-phenylsulfanyl)-phenyl]-2(R)-methyl-piperazin-1-yl}-acetic acid {4-[2-(4-Methoxy-phenylsulfanyl)-phenyl]-2(R),5(S)-dimethyl-piperazin-1-yl}-acetic acid {4-[5-Chloro-2-(4-methoxy-phenylsulfanyl)-phenyl]-2,2-dimethyl-piperazin-1-yl}-acetic acid (+/−)-{4-[5-Chloro-2-(4-trifluoromethyl-phenylsulfanyl)-phenyl]-2-methyl-piperazin-1-yl}-acetic acid {4-[5-Chloro-2-(3-methoxy-phenylsulfanyl)-phenyl]-2(R)-methyl-piperazin-1-yl}-acetic acid (+/−)-{4-[2-(4-Phenyl-phenyloxy)-phenyl]-2-methyl-piperazin-1-yl}-acetic acid (+/−)-{4-[2-(4-Methyl-phenylsulfanyl)-phenyl]-trans-2,5-dimethyl-piperazin-1-yl}-acetic acid (+/−)-{4-[2-(4-iso-Propyl-phenylsulfanyl)-phenyl]-trans-2,5-dimethyl-piperazin-1-yl}-acetic acid (+/−)-{4-[2-(2,4-Dimethyl-phenylsulfanyl)-phenyl]-trans-2,5-dimethyl-piperazin-1-yl}-acetic acid (+/−)-2-{4-[2-(4-tert-Butyl-phenylsulfanyl)-phenyl]-3-methylpiperazin-1-yl}-propionic acid {4-[2-(4-Isopropyl-phenylsulfanyl)-phenyl]-piperazin-1-yl}-acetic acid (+/−)-2-{4-[2-(4-Methoxy-phenylsulfanyl)-phenyl]-3-methyl-piperazin-1-yl}-propionic acid or a pharmaceutically acceptable acid addition salt thereof.

Definition of Substituents

Halogen means fluoro, chloro, bromo or iodo.

The expression $C_{1-6}$-alk(en/yn)yl means a $C_{1-6}$-alkyl, $C_{2-6}$-alkenyl, or a $C_{2-6}$-alkynyl group. The expression $C_{3-8}$-cycloalk(en)yl means a $C_{3-8}$-cycloalkyl- or cycloalkenyl group.

The term $C_{1-6}$ alkyl refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and one triple bond respectively, including but not limited to ethenyl, propenyl, butenyl, ethynyl, propynyl and butynyl.

The term $C_{3-8}$ cycloalkyl designates a monocyclic or bicyclic carbocycle having three to eight C-atoms, including but not limited to cyclopropyl, cyclopentyl, cyclohexyl, etc.

The term $C_{3-8}$ cycloalkenyl designates a monocyclic or bicyclic carbocycle having three to eight C-atoms and including one double bond.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

The terms $C_{1-6}$-alk(en/yn)yloxy, $C_{1-6}$ alk(en/yn)ylsulfanyl, hydroxy-$C_{1-6}$-alk(en/yn)yl, halo-$C_{1-6}$-alk(en/yn)yl, halo-$C_{1-6}$-alk(en/yn)yloxy, $C_{1-6}$-alk(en/yn)ylsulfonyl etc. designate such groups in which the $C_{1-6}$-alk(en/yn)yl are as defined above.

As used herein, the term $C_{1-6}$-alk(en/yn)yloxycarbonyl refers to groups of the formula $C_{1-6}$-alk(en/yn)yl-O—CO—, wherein $C_{1-6}$-alk(en/yn)yl are as defined above.

As used herein, the term acyl refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$-alk(en/yn)yl-carbonyl group.

The term 3–7-membered ring optionally containing one further heteroatom as used herein refers to ring systems such as 1-morpholinyl, 1-piperidinyl, 1-azepinyl, 1-piperazinyl, 1-homopiperazinyl, 1-imidazolyl, 1-pyrrolyl, or 1-pyrazolyl, all of which may be further substituted with $C_{1-6}$-alkyl.

The term heteroaryl may represent 5-membered monocyclic rings such as 3H-1,2,3-oxathiazole, 1,3,2-oxathiazole, 1,3,2-dioxazole, 3H-1,2,3-dithiazole, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene and 6-membered monocyclic rings such as 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 1H-1,2,3-oxadiazine, 2H-1,2,4-oxadiazine, 2H-1,2,5-oxadiazine, 2H-1,2,6-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazine, pyrazine, pyridazine, pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

The term aryl refers to carbocyclic, aromatic systems such as phenyl and naphtyl.

The acid addition salts of the invention are preferably pharmaceutically acceptable salts of the compounds of the invention formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers or diastereomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic, compounds of the present invention can also be resolved into their optical antipodes, e.g. by fractional crystallization of d- or l-(tartrates, mandelates or camphorsulphonate) salts. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

Pharmaceutical Compositions

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine: Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg. The total daily dose is usually in the range of about 0.05–500 mg, and most preferably about 0.1 to 50 mg of the active compound of the invention.

The compounds of the invention are prepared by the following general methods: Alkylation of an amine of formula II with an alkylating agent of formula III

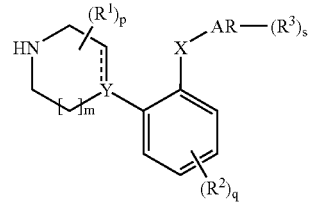
(II)

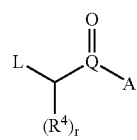
(III)

L is a suitable leaving group such as halogen or tosylate. The substituents AR, $R^1$-$R^4$, Y, Q, X, A, m, p, q, r and s are as defined above. The reaction is typically performed in a suitable solvent such as ethanol, N,N-dimethylformamide or acetonitrile containing an inorganic base such as potassium or cesium carbonate or an organic base such N-ethyl diisopropylamine at an elevated temperature of 40–120° C. Compounds of formula I wherein Q is carbon and A is $OR^6$ wherein $R^6$ is hydrogen may be prepared from the corresponding esters $COOR^6$ wherein $R^6$ is an insoluble polymer or $C_{1-6}$-alkyl, aryl or aryl-$C_{1-6}$-alkyl. The transformation may be performed under basic conditions, for example, using aqueous sodium hydroxide in an alcoholic solvent or acidic conditions for $R^6$ being a tertiary-butyl group or an insoluble polymer.

Compounds of Formula II May be Prepared by any of the Following Reactions:

a) Chemical transformation of a compound with formula IV

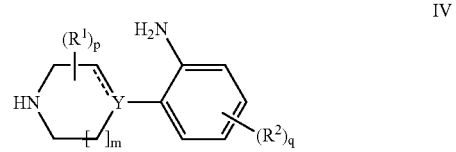
IV wherein $R^1$, $R^2$, m, p, q, X, Y and Z are as described above, to the corresponding diazonium compound, and subsequently react with a compound HX-AR-$(R^3)_s$, wherein AR, X, $R^3$ and s are as defined above.

b) A chemical synthesis as depicted in scheme I

Scheme I

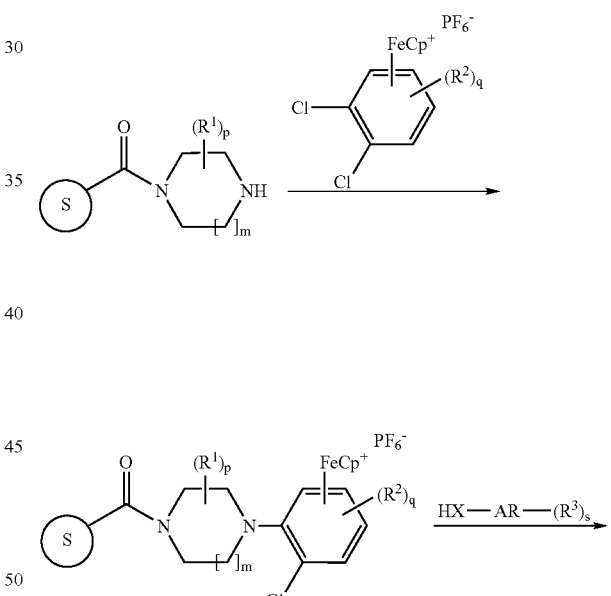

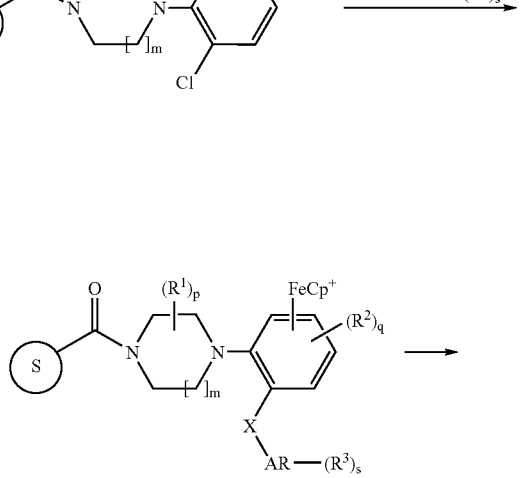

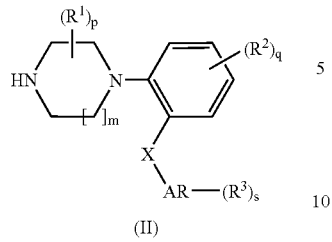

(II)

wherein AR, $R^1$, $R^2$, $R^3$, s, m, p, q and X are as described above and the circled S represents the solid support.

c) A chemical synthesis as depicted in scheme II where X is O and Y is N.

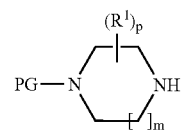

VI wherein $R^1$, m and p are as defined above.

e) Dehydrating and optionally simultaneously deprotecting a compound of formula VII Scheme II

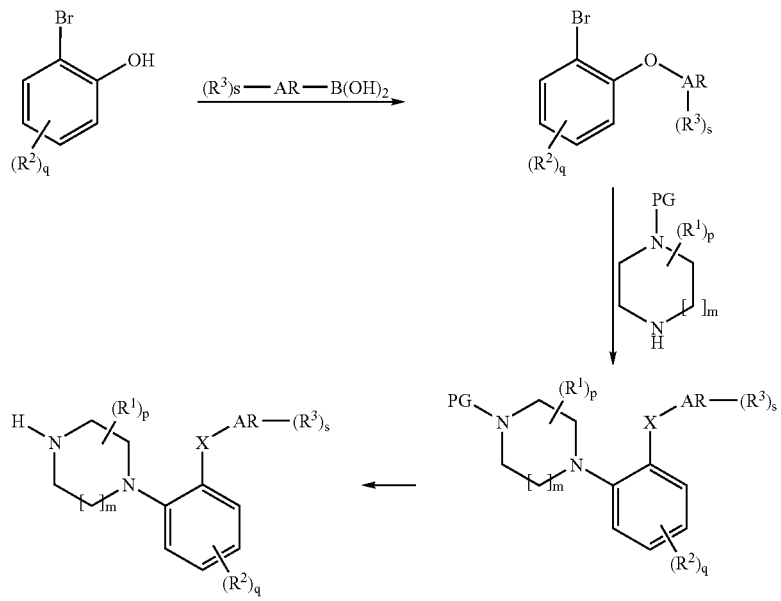

d) A chemical transformation of a compound of formula V

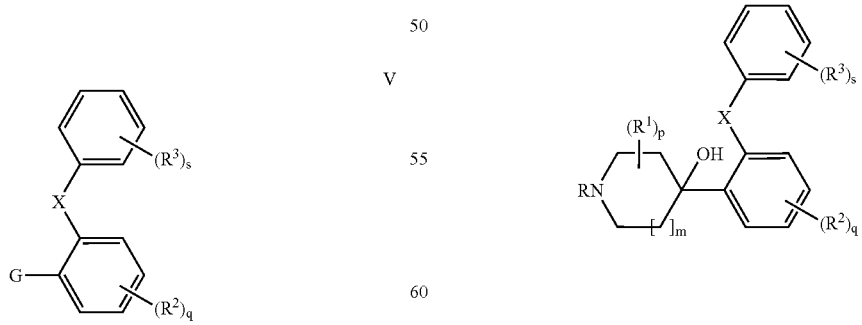

V wherein $R^2$, $R^3$, X, s and q are as described above and G is a bromine or iodine atom with a compound of formula VI

VII wherein $R^1$, $R^2$, $R^3$, X, m, p, q and s are as described above and R is either a hydrogen atom or a BOC group.

f) Hydrogenation of the double bond in a compound of formula VIII

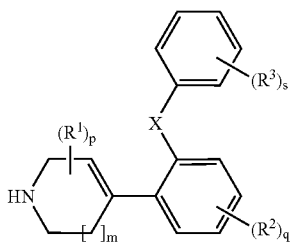

wherein $R^1$, $R^2$, $R^3$, X, m, p, q and s are as described above.
g) Deoxygenation and deprotection of a compound of formula VII

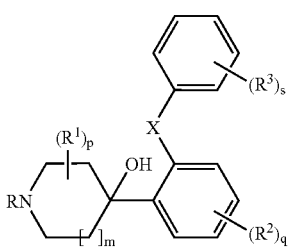

wherein $R^1$, $R^2$, $R^3$, X, m, p, q and s are as described above and R is either a hydrogen atom or a BOC group.

The diazotation followed by reaction with a compound HS—Ar—$(R_3)_s$ according to method a) is performed by addition of the diazonium salt of the corresponding aniline to a solution of sodium salt of a thiophenol in water containing a copper suspension. The starting material of formula IV is prepared as outlined in the following. A fluoronitrobenzene derivative is reacted with a piperazine derivative in a solvent such as DMF, NMP or other dipolar aprotic solvent containing an organic base such as triethylamine to afford the orthonitrophenylpiperazine derivative. The nitro group is then reduced using standard procedures known to those skilled in the art to give the starting material of formula IV.

For 2,5-dimethylpiperazine derivatives the N-Benzyl-2(R),5(S)-dimethylpiperazine was prepared according to known literature procedures (Aicher et al *J. Med. Chem.* 2000, 43, 236–249). N-Benzyl-2(S),5(R)-dimethylpiperazine was prepared according to patent application WO 00/71535.

The reaction sequence in method b) is prepared according to the methods described in patent application WO 01/49681. The diamines are either commercially available or synthesised by methods known to chemists skilled in the art. Iron-complexes, like $\eta^6$-1,2-dichlorobenzene-$\eta^5$-cyclopentadienyliron(II) hexafluorophosphate and substituted analogues are synthesised according to literature known procedures (Pearson et al. *J. Org. Chem.* 1996, 61, 1297–1305) or synthesised by methods known to chemists skilled in the art.

The starting material in method c) is prepared by the coupling of an ortho bromophenol with a suitable arylboronic acid or boronate ester in a known literature procedure (Evans et al, *Tet. Lett*, 1998, 39, 2947–2940). The resulting biarylether bromide is then coupled using palladium catalysis to a protected piperazine where the protective group may be typically but not exclusively a tert-butyloxycarbonyl (BOC) derivative or benzyloxycarbonyl (CBZ) and the protecting group (PG) is then removed by acidic cleavage for example using hydrogen chloride in an alcoholic solvent for removal of the BOC group or catalytic hydrogenolysis in the case of the a CBZ removed to give intermediates of formula II where X is O and Y is N. The general methods for removal of suitable protecting groups are described in the textbook *Protective Groups in Organic Synthesis* T. W. Greene and P. G. M. Wuts, Wiley Interscience, (1991) ISBN 0471623016.

The reaction of a compound of formula V with a diamine of formula VI in method d) was performed in a similar manner as described in Nishiyama et al. *Tetrahedron Lett.* 1998, 39, 617–620. The starting material of formula VI was prepared in a similar manner as described in Schopfer et al. *Tetrahedron* 2001, 57, 3069–3073.

The dehydration reaction and optional simultaneous deprotection of a compound of formula VII in method e) was performed in a similar manner as described in Palmer et al *J. Med. Chem.* 1997, 40, 1982–1989. The starting material of formula VII was prepared from a compound of formula VII wherein R is a BOC group by deprotection with hydrochloric acid in methanol. Compounds of formula VII may be prepared as described in Palmer et al. *J. Med. Chem.* 1997, 40, 1982–1989.

The reduction of the double bond according to method f) is generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran (THF), dioxane, or diethyl ether.

The deoxygenation of tertiary alcohol intermediates of formula VII in method g) wherein R is a BOC group, was performed by a modified Barton reduction in a similar manner as described in Hansen et al. *Synthesis* 1999, 1925–1930. The intermediate tertiary alcohols were prepared from the corresponding properly substituted 1-bromophenylsulfanylbenzenes or their corresponding ethers by metal-halogen exchange followed by addition of an appropriate electrophile of the formula IX in a similar manner as described in Palmer et al. *J. Med. Chem.* 1997, 40, 1982–1989. The properly substituted 1-bromo-phenylsulfanylbenzenes were prepared in a similar manner as described in the literature by reaction of properly substituted thiophenols with properly substituted aryliodides according to Schopfer and Schlapbach *Tetrahedron* 2001, 57 3069–3073 Bates et al., *Org. Lett.* 2002, 4, 2803–2806 and Kwong et al. *Org. Lett.* 2002, 4, (in press). The corresponding substituted 1-bromo-phenoxybenzenes may be prepared as described by Buck et al. *Org. Lett.* 2002, 4, 1623–1626. Removal of the BOC group was performed by standard methods known to those skilled in the art

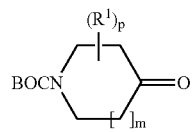

EXAMPLES

General Methods

Analytical LC-MS data were obtained on a PE Sciex API 150EX instrument equipped with IonSpray source and Shimadzu LC-8A/SLC-10A LC system. Column: 30×4.6 mm Waters Symmmetry C18 column with 3.5 µm particle size; Solventsystem: A=water/trifluoroacetic acid (100:0.05) and B=water/acetonitrile/trifluoroacetic acid (5:95:0.03); Method: Linear gradient elution with 90% A to 100% B in 4 min and with a flow rate of 2 mL/min. Purity was determined by integration of the UV (254 nm) and ELSD trace. The retention times (RT) are expressed in minutes.

Preparative LC-MS-purification was performed on the same instrument. Column: 50×20 mm YMC ODS-A with 5 µm particle size; Method: Linear gradient elution with 80% A to 100% B in 7 min and with a flow rate of 22.7 mL/min. Fraction collection was performed by split-flow MS detection.

$^1$H NMR spectra were recorded at 500.13 MHz on a Bruker Avance DRX500 instrument or at 250.13 MHz on a Bruker, AC 250 instrument. Deuterated methylenehloride (99.8% D), chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and b=broad singlet.

For ion-exchange chromatography, the following material was used: SCX-columns (1 g) from Varian Mega Bond Elut®, Chrompack cat. No. 220776. Prior to use, the SCX-columns were pre-conditioned with 10% solution of acetic acid in methanol (3 mL). For de-complexation by irradiation, a ultaviolet light source (300 W) from Philipps was used. As starting polymer supports for solid phase synthesis, Wang-resin (1.03 mmol/g, Rapp-Polymere, Tuebingen, Germany) was used.

Preparation of Intermediates of Formula IV 2-(3-Methylpiperazin-1-yl)phenylamine 2-Fluoronitrobenzene (7.1 g, 50 mmol) was dissolved in DMF (100 mL) containing triethylamine (10 g, 100 mmol) and placed under a nitrogen atmosphere. To the reaction was added 2-methylpiperazine (5.0 g, 50 mmol). The reaction was heated to 80° C. for 16 hours. The reaction was allowed to cool to room temperature before the solvent was reduced to half volume in vacuo. Ethyl acetate (200 mL) and ice-water (250 mL) were added to the solution and the product was extracted with diethylether (2×200 mL). The aqueous phase was saturated with sodium chloride and extracted with ethyl acetate (2×200 mL). The organic phases were combined, washed with saturated brine, dried over magnesium sulfate, filtered and the filtrate was concentrated in vacuo. The product (10.5 g) was dissolved in ethanol (250 mL). Palladium on charcoal catalyst (10% w/w, 2.2 g) was added to the solution and the solution was hydrogenated in a Parr apparatus at 3 bar for 3 hours. The solution was filtered and evaporated to give the aniline product. Yield (8.0 g, 83%)

The following intermediates were prepared in an analogous fashion:
2-(3,5-Dimethylpiperazin-1-yl)phenylamine
2-(3,3-Dimethylpiperazin-1-yl)phenylamine
4-Methoxy-2-(3-methylpiperzin-1-yl)phenylamine 2-(2(S),5(R)-Dimethylpiperazin-1-yl)phenylamine 2(R),5(S)-Dimethyl-1-N-benzyl-piperazine (6.0 g, 29 mmol) was dissolved in dimethylformamide (100 mL), and triethylamine (6.4 mL, 44 mmol) and the mixture was placed under nitrogen. To the solution was added 2-fluoro-nitrobenzene (3.5 mL, 31 mmol). The reaction was heated at 100° C. for 72 hours The solution was evaporated in vacuo and redissolved in ethyl acetate (100 mL). The solution was then washed with saturated sodium bicarbonate solution (100 mL) and saturated brine solution (100 mL). The separated organic phase was dried over magnesium sulfate, filtered and the filtrate was evaporated in vacuo. The crude product was then purified by flash chromatography, eluting with ethyl acetate/methanol/triethylamine 85:10:5. The product (8.2 g) was dissolved in ethanol (250 mL). Palladium on charcoal catalyst (10% w/w, 2.2 g) was added to the solution and the solution was hydrogenated in a Parr apparatus at 3 bar for 3 hours. The solution was filtered and evaporated to give the aniline product. Yield (5.2 g, 87%)

The following intermediate were prepared in an analogous fashion
2-(2(S),5(R))-Dimethylpiperazin-1-yl)phenylamine 4-Chloro-2-(3,3-dimethyl-piperazin-1-yl)-phenylamine 2,2-Dimethylpiperazine (9.55 g, 84 mmol) was dissolved in dimethylformamide (140 mL). To the solution was added triethylamine (12.07 mL, 83.6 mmol) and the reaction was placed under a nitrogen atmosphere. The solution was heated to 80° C. and 4-Chloro-2-fluoro-nitrobenzene (13.5 g, 76 mmol) was added as a solution in dimethylformamide (35 mL). The reaction was stirred at 40° C. for 16 hours. The solvent was removed in vacuo and the residue dissolved in ethanol (250 mL). Ammonium chloride (28 g) and zinc powder (17 g) were added. The reaction was boiled under reflux at 80° C. for 1 hour and then allowed to stir at 40° C. for 72 hours. The reaction was then filtered and the filtrate evaporated in vacuo. The solid was then washed with ethyl acetate and then a small amount of methanol-Yield: 16.04 g, 88%

The following intermediates were prepared in an analogous fashion
4-Chloro-2-(3-(R)-methyl-piperazin-1-yl)-phenylamine
4-Chloro-2-(3-(S)-methyl-piperazin-1-yl)-phenylamine

Preparation of Intermediates of Formula II by Method a

1-[2-(4-Chloro-phenylsulfanyl)phenyl]-3-methylpiperazine 2-(3-Methylpiperazin-1-yl)phenylamine (0.96 g, 5 mmol) was dissolved in water (30 mL) containing concentrated sulfuric acid (0.28 mL, 5.2 mmol), the solution was cooled to 0° C. and sodium nitrite (0.36 g, 5.2 mmol) was added. The reaction was stirred for 30 minutes before the pH of the reaction was adjusted to pH 7 with sodium acetate. The diazonium salt solution was then added dropwise to a solution of 4-chlorothiophenol in 2 M NaOH (4 mL) containing a copper suspension (0.3 g, 5 mmol). After addition, the mixture was heated to 60° C. for 30 minutes before being allowed to cool to room temperature and ethyl acetate (10 mL) was added. The mixture was filtered and the organic layer was separated. The aqueous layer was extracted with ethyl acetate (2×10 mL). The combined organic extracts were dried over magnesium sulfate, filtered and evaporated in vacuo. The crude product was purified by flash chromatography using silica gel, eluting with ethyl acetate/methanol/ammonia 96:3:1. The pure product was isolated as a colourless oil. Yield (0.18 g, 11%) $^1$H NMR (CDCl$_3$, 500 MHz) 1.12 (d, 3H); 2.6–2.72 (br m, 2H); 3.0–3.15 (m, 5H); 6.9 (m, 2H); 7.08 (d, 1H); 7.15 (m, 1H); 7.25–7.35 (m, 4H); MS (MH$^+$) 319.1.

The following compounds were prepared in an analogous fashion:
1-[2-(4-Chloro-phenlsulfanyl)phenyl]-3,5-dimethylpiperazine
(+/−)-{4-[2-(4-Methoxy-phenylsulfanyl)-phenyl]-trans-2,5-dimethyl-piperazine
(+/−)-{4-[2-(4-Chloro-phenylsulfanyl)-phenyl]-trans-2,5-dimethyl-piperazine
(+/−)-{4-[2-(4-tert-Butyl-phenylsulfanyl)-phenyl]-trans-2,5-dimethyl-piperazine
(+/−)-(4-[2-(4-Fluoro-phenylsulfanyl)-phenyl]-trans-2,5-dimethyl-piperazine
(+/−)-4-[2-(4-tert-Butyl-phenylsulfanyl)-phenyl]-2-methyl-piperazine
(+/−)-4-[2-(4-iso-Propyl-phenylsulfanyl)-phenyl]-2-methyl-piperazine
4-[5-Chloro-2-(4-methoxy-phenylsulanyl)-phenyl]-2(R)-methyl-piperazine
4-[2-(4-Methoxy-phenylsulfanyl)-phenyl]-2(R),5(S)-dimethyl-piperazine.

Preparation of Intermediates II According to Method b where A Represents an Insoluble Polymer Preparation of Iron Complexes η$^6$-1,2-Dichlorobenzene-η$^5$-cyclopentadienyliron(II) hexafluorophosphate Ferrocene (167 g), anhydrous aluminium trichloride (238 g) and powdered aluminium (24 g) were suspended in 1,2-dichlorobenzene (500 mL) and heated to 90° C. in a nitrogen atmosphere for 5 h with intensive stirring. The mixture was cooled to room temperature and water (1000 mL) was added carefully in small portions while cooling on an ice bath. Diethylether (500 mL) were added, and the mixture was stirred at room temperature for 30 minutes. The mixture was extracted with diethylether (3×300 mL). The aqueous phase was filtered, and aqueous ammonium hexafluorophosphate (60 g in 50 mL water) was added in small portions under stirring. The product was allowed to precipitate at room temperature. After 3 hours the precipitate was filtered off, washed intensively with water and dried in vacuo (50° C.) to give 81 g (21%) of the title compound as a light yellow powder. $^1$H NMR (D$_6$-DMSO): 5.29 (s, 5H); 6.48 (m, 2H); 7.07 (m, 2H).

Preparation of Polystyrene-bound Amines

4-[(piperazin-1-yl)carbonyloxymethyl]phenoxymethyl polystyrene

4-[(4-Nitrophenoxy)carbonyloxymethyl]phenoxymethyl polystyrene (267 g, 235 mmol) was suspended in dry N,N-dimethylformamide (2 L). N-Methylmorpholine (238.0 g, 2.35 mol) and piperazine (102.0 g, 1.17 mol) were added and the mixture was stirred at room temperature for 16 h. The resin was filtered off and washed with N,N-dimethylformamide (2×1 L), tetrahydrofuran (2×1 L), water (1×500 mL), methanol (2×1 L), tetrahydrofuran (2×1 L) and methanol (1×1 L). Finally, the resin was washed with dichloromethane (3×500 mL) and dried in vacuo (25° C., 36 h) to yield an almost colourless resin (240.0 g).

The following polystyrene bound diamines were prepared analogously:
4-[(2,5-Dimethyl-piperazin-1-yl)carbonyloxymethyl]phenoxymethyl polystyrene
4-[(3-Methyl-piperazin-1-yl)carbonyloxymethyl]phenoxymethyl polystyrene Preparation of Resin-Bound η$^6$-aryl-η$^5$-cyclopentadienyliron(II) hexafluorophosphates 4-({4-[η$^6$-(2-Chlorophenyl)-η$^5$-cyclopentadienyliron(II)]piperazin-1-yl}carbonyloxymethyl)phenoxymethyl polystyrene hexafluorophosphate 4-[(piperazin-1-yl)carbonyloxymethyl]phenoxymethyl polystyrene (115.1 g, 92 mmol) was suspended in dry tetrahydrofuran (1.6 L), and η$^6$-1,2-dichlorobenzene-η$^5$-cyclopentadienyliron(II) hexafluorophosphate (76.0 g, 184 mmol) was added followed by potassium carbonate (50.9 g, 368 mmol). The reaction mixture was stirred at 60° C. for 16 h. After cooling to room temperature, the resin was filtered off and washed with tetrahydrofuran (2×500 mL), water (2×250 mL), tetrahydrofuran (2×500 mL), water (2×250 mL), methanol (2×250 mL), dichloromethane (2×250 mL) and methanol (2×250 mL). Finally, the resin was washed with dichloromethane (3×500 mL) and dried in vacuo (25° C., 36 h) to yield a dark orange resin (142 g).

The following polystyrene bound iron-complexes were prepared analogously:
4-({4-[η$^6$-(2-Chlorophenyl)-η$^5$-cyclopentadienyliron(II)]-2,5-dimethylpiperazin-1-yl}carbonyloxymethyl)phenoxymethyl polystyrene hexafluorophosphate
4-({4-[η$^6$-(2-Chlorophenyl)-η$^5$-cyclopentadienyliron(II)]-3-methylpiperazin-1-yl}carbonyloxymethyl)phenoxymethyl polystyrene hexafluorophosphate Preparation of ortho-(arylsulfanyl)phenyl piperazines (+/−)-1-[2-(4-Methylphenylsulfanyl)phenyl]-trans-2,5-dimethylpiperazine:

To a solution of 4-methylthiophenol (1.4 g, 9.8 mmol) in a 1:1 mixture of tetrahydrofuran/dimethylformamide (5 mL), sodium hydride (7.4 mmol, 60% in mineral oil) was carefully added at room temperature (Caution: Generation of hydrogen). The mixture was stirred for an additional 30 min after the generation of hydrogen had ceased. Subsequently, 4-({4-[η$^6$-(2-chloro-phenyl)-η$^5$-cyclopentadienyliron(II)]-trans-2,5-dimethyl-piperazin-1-yl}carbonyloxymethyl)phenoxymethyl polystyrene hexafluorophosphate (3.5 g, 2.45 mmol) was added and the mixture was stirred at 55° C., for 6 h. After cooling to room temperature, the resin was filtered off and washed with tetrahydrofuran (2×50 mL), tetrahydrofuran/water (1:1) (2×50 mL), N,N-dimethylformamide (2×50 mL), water (2×50 mL), methanol (3×50 mL), tetrahydrofuran (3×50 mL), and subsequently with methanol and tetrahydrofuran (each 50 mL, 5 cycles). Finally, the resin was washed with dichloromethane (3×50 mL) and dried in vacuo (25° C., 12 h) to yield a dark orange resin. The thus obtained resin and a 0.5 M solution of 1,10-phenanthroline in 3:1 mixture of pyridine/water (20 mL) was placed in light-transparent reactor tube. The suspension was agitated by rotation under irradiation with visible light for 12 h. The resin was filtered and washed with methanol (2×25 mL), water (2×25 mL) and tetrahydrofuran (3×25 mL) until the washing solutions were colourless (approx. 5 cycles) and the irradiation procedure was repeated until decomplexation was complete (approx. 5 cycles). After the decomplexation was completed, the resin was washed with dichlormethane (3×25 mL) and dried in vacuo (25° C., 12 h) to obtain a light brown resin. 3.7 g (24 mmol) of the thus obtained resin were suspended in a 1:1 mixture of trifluoroacetic acid and dichlormethane (2 mL) and stirred at room temperature for 2.5 h. The resin was filtered off and washed with dichloromethane (5×0.5 mL). After evaporation of the filtrate from volatile solvents in vacuo, an orange oil was obtained. The crude product was purified by preparative LC-MS and subsequently by ion-exchange chromatography.

LC/MS (m/z) 313.2 (MH$^+$); RT=2.17; purity (UV, ELSD): 87.1%, 98.7%; yield: 47.8 mg (6%).

The following arylpiperazines were prepared analogously:

(+/−)-1-[2-(4-Isopropylphenylsulfanyl)phenyl]-trans-2,5-dimethylpiperazine (+/−)-1-[2-(2,4-Dimethylphenylsulfanyl)phenyl]-trans-2,5-dimethylpiperazine (+/−)-1-[2-(4-Tertbuytylphenylsulfanyl)phenyl]-trans-2,5-dimethyl-piperazine (+/−)-1-[2-(4-Methoxy-phenylsulfanyl)-phenyl]-2-methylpiperazine (+/−)-1-[2-(4-Isopropyl-phenylsulfanyl)-phenyl]-piperazine.

Preparation of Intermediates of Formula III where A is an Insoluble Polymer

4-[Chloroacetoxymethyl]phenoxymethyl polystyrene

Wang resin (10 g, 10.3 mmol) was suspended in dichloromethane (100 mL) and cooled to 0° C. Diisopropylethylamine (9 mL, 52 mmol) was added. Chloroacetylchloride was added slowly. The reaction mixture was stirred at 0° C. for 30 min and then allowed to heat to room temperature. The reaction mixture was stirred at room temperature for 16 h. The resin was filtered off and washed with N,N-dimethylformamide (3×100 mL), dichloromethane (2×100 mL), dimethylformamide (3×100 mL) and dichloromethane (2×100 mL) and dried in vacuo (25° C., 16 h).

The following resin was prepared in an analogous fashion:

4-[2-Chloropropionyloxymethyl]phenoxymethyl polystyrene

Preparation of Intermediates II by Method c 4-(2-Bromo-phenoxy)-biphenyl

A mixture of 2-bromophenol (2.08 g, 12 mmol), 4-biphenylboronic acid (4.75 g, 24 mmol), Cu(OAc)$_2$ (2.20 g, 12 mmol) and triethylamine (6.1 g, 60 mmol) in dioxane (100 mL) was stirred for 48 h. The crude mixture was evaporated onto silica gel and purified by column chromatography eluting with ethyl acetate/heptane 1:9. Yield: 0.73 g (19%). $^1$H NMR (CDCl$_3$, 500 MHz) 7.65 (m, 1H) 7.55 (m, 4H), 7.43 (m, 2H), 7.25–7.38 (m, 2H), 7.00–7.08 (m, 4H); MS(m/z): 325.1.

(+/−)-1-[2-(Biphenyl-4-yloxy)-phenyl]-3-methyl-piperazine

A mixture of 4-(2-bromo-phenoxy)-biphenyl (0.73 g, 2.25 mmol), rac-2-methylpiperazine (0.285 g, 0.285 mmol), Pd$_2$dba$_3$ (0.022 g, 1 mol %), rac-binap (0.043 g, 3 mol %) and NaOBu$^t$ (0.300 g, 3.12 mmol) in dry toluene (15 mL) under argon and stirred at 90° C. overnight. After cooling to room temperature the mixture is filtered and evaporated onto silica gel and and purified by column chromatography eluting with ethyl acetate/heptane 1:2. Yield: 0.264 g (34%). $^1$H NMR (CDCl$_3$, 500 MHz) 7.55 (m, 2H), 7.49 (m, 2H), 7.38 (m, 2H), 7.27 (m, 1H), 7.10 (m, 1H), 6.90–7.00 (m, 5H), 3.30–3.35 (m, 2H), 2.88 (m, 1H), 2.62–2.80 (m, 3H), 2.30–2.40 (m, 1H) 1.60–2.00 (br, 1H), 0.99 (d, 3H); MS(m/z): 345.1.

Preparation of Compounds of the Invention

Example 1

1a (+/−)-{4-[2-(4-Methoxy-phenylsulfanyl)-phenyl]-trans-2,5-dimethyl-piperazin-1-yl}-acetic acid, hydrochloride 4-[2-(4-Methoxyphenylsulfanyl)-phenyl]-trans-2,5-dimethyl-piperazine (0.5 g, 1.5 mmol) and N-ethyldisopropylamine (0.315 mL, 1.8 mmol) was dissolved in acetonitrile (10 mL) and placed under a nitrogen atmosphere. Ethyl bromoacetate (0.19 mL, 1.7 mmol) was added and the mixture was stirred at ambient temperature for 16 hours. To the mixture was then added a small amount of silica gel and the solvent was evaporated in vacuo. The product, absorbed on to silica gel, was poured on to a silica cartridge and eluted with dichloromethane/heptane/ethyl acetate (60:35:5). The ester was isolated from relevant fractions as a light oil (300 mg, 48%). The ester was then dissolved in ethanol (10 mL) and 2N NaOH was added (5 mL). The reaction was stirred for 16 hours at room temperature. The reaction was evaporated in vacuo and the residue was dissolved in ethyl acetate (50 mL). 2N HCl (15 mL) was added and the phases were separated. The aqueous phase was reextracted with ethyl acetate (2×50 mL). The combined organic fractions were dried (MgSO$_4$), filtered and evaporated. The residue was dissolved in a small amount of dichloromethane, precipitated by the addition of heptane and the solvent was removed in vacuo. Yield (280 mg, 100%). $^1$H NMR (CDCl$_3$, 500 MHz) 0.87 (d, 3H), 1.35 (d, 3H), 3.04 (m, 1H), 3.12 (m, 2H), 3.6 (m, 3H), 4.11 (d, 1H), 4.31(d, 1H), 3.81 (s, 3H), 6.55 (d, 1H), 7.02 (d, 2H), 7.13 (dd, 1H), 7.2 (m, 1H), 7.42 (d, 2H), LC-MS (m/z) (MH)$^+$ 387.4 RT=2.22 (UV, ELSD) 98%, 97% and the following compounds were prepared in an analogous fashion:

1b (+/−)-{4-[2-(4-Chloro-phenylsulfanyl)-phenyl]-trans-2,5-dimethyl-piperazin-1-yl}-acetic acid, hydrochloride $^1$H NMR (CDCl$_3$, 500 MHz) 0.80 (d, 3H), 1.28 (d, 3H), 2.92–3.18 (m, 3H), 3.64 (m, 3H), 4.06 (d, 1H), 4.29 (d, 1H), 6.78 (d, 1H), 7.12 (t, 1H), 7.26 (m, 2H), 7.50 (m, 4H), LC-MS (m/z) (MH$^+$) 391.2 RT=2.43 (UV, ELSD) 99%, 99%. Yield 420 mg.

1c (+/−)-{4-[2-(4-tert-Butyl-phenylsulfanyl)-phenyl]-trans-2,5-dimethyl-piperazin-1-yl}-acetic acid, hydrochloride $^1$H NMR (CDCl$_3$, 500 MHz) 0.76 (d, 3H), 1.01 (d, 3H), 1.30 (s, 9H), 2.4–2.6 (m, 2H), 2.9–3.0 (m, 3H), 3.28 (m, 1H), 3.32 (d, 1H), 3.48 (d, 1H), 6.65 (d, 1H), 7.01 (t, 1H), 7.13 (t, 1H), 7.24 (d, 1H), 7.39 (d, 2H), 7.47 (d, 2H), LC-MS (m/z) (MH$^+$) 412.9 RT=2.70 (UV, ELSD) 95%, 99%. Yield 550 mg.

1d (+/−)-(4-[2-(4-Fluoro-phenylsulfanyl)-phenyl]-trans-2,5-dimethyl-piperazin-1-yl}-acetic acid, hydrochloride $^1$H NMR (CDCl$_3$, 500 MHz) 0.80 (d, 3H), 1.25 (d, 3H), 2.8–3.0 (m, 2H), 3.08 (m, 1H), 3.4–3.6 (m, 3H), 3.87 (d, 1H), 4.06 (d, 1H), 6.64 (d, 1H), 7.07 (m, 1H), 7.20 (m, 1H), 7.26 (m, 1H), 7.32 (dd, 2H), 7.54 (dd, 2H), LC-MS (m/z) (MH$^+$) RT=2.24 (UV, ELSD) 95%, 99%. Yield 180 mg.

1e (+/−)-{4-[2-(4-tert-Butyl-phenylsulfanyl)-phenyl]-2-methyl-piperazin-1-yl}-acetic acid, hydrochloride LC/MS (m/z) 399.2 (MH$^+$); RT=2.54; purity (UV, ELSD): 100%, 100%; yield: 10.4 mg.

1f (+/−)-{4-[2-(4-iso-Propyl-phenylsulfanyl)-phenyl]-2-methyl-piperazin-1-yl}-acetic acid, hydrochloride LC/MS (m/z) 385.1 (MH$^+$); RT=2.45; purity (UV, ELSD): 88%, 100%; yield: 11 mg.

1g (+/−)-2-(4-[2-(4-tert-Butyl-phenylsulfanyl)-phenyl]-trans 2,5 dimethylpiperazin-1-yl)-propionic acid, hydrochloride LC/MS (m/z) 427.0 (MH$^+$); RT=2.76; purity (UV, ELSD): 86%, 98%; yield: 27 mg.

1h (4-[5-Chloro-2-(4-methoxy-phenylsulfanyl)-phenyl-2(R)-methyl-piperazin-1-yl}-acetic acid, hydrochloride $^1$H NMR (DMSO, 500 MHz) 1.40 (d, 3H), 3.16 (m, 1H), 3.25–3.48 (m, 4H), 3.63 (m, 1H), 3.75 (m, 1H), 3.80 (s, 3H), 4.15 (d, 1H), 4.30 (d, 1H) 6.55 (d, 1H), 7.02 (d, 2H), 7.13 (dd, 1H), 7.2 (m, 1H), 7.42 (d, 2H)

LC/MS (m/z) 407.3 (MH$^+$); RT=2.79; purity (UV, ELSD): 95%, 100%; yield: 225 mg.

1i {4-[2-(4-Methoxy-phenylsulfanyl)-phenyl]-2(R), 5(S)-dimethyl-piperazin-1-yl}-acetic acid, hydrochloride $^1$H NMR (DMSO-d6, 500 MHz) 0.85 (d, 3H), 1.30 (d, 3H), 2.95 (t, 1H), 3.05 (m, 2H) 3.53 (d, 1H), 3.60–3.65 (m, 2H), 3.80 (m, 3H), 3.92 (d, 1H), 4.10 (d, 1H), 6.55 (d, 1H), 7.02 (d, 2H), 7.13 (dd, 1H), 7.2 (m, 1H), 7.42 (d, 2H)

LC/MS (m/z) 387.3 (MH$^+$); RT=2.22; purity (UV, ELSD): 97%, 96.9%; yield: 607 mg.

1j {4-[5-Chloro-2-(4-methoxy-phenylsulfanyl)-phenyl]-2,2-dimethyl-piperazin-1-yl}-acetic acid, hydrochloride $^1$H NMR (DMSO-d6, 500 MHz) 1.58 (s, 6H), 3.20 (s, 2H), 3.20–3.60 (br m, 4H), 3.80 (s, 3H), 3.92 (d, 1H), 4.10 (d, 1H), 6.55 (d, 1H), 6.90 (dd, 1H), 6.96 (d, 2H), 7.13 (s, 1H), 7.40 (d, 2H)

LC/MS (m/z) 421.1 (MH$^+$); RT=2.41; purity (UV, ELSD): 96%, 98%; yield: 1.18 g.

1k {4-[5-Chloro-2-(4-trifluoromethyl-phenylsulanyl)-phenyl]-2-methyl-piperazin-1-yl}-acetic acid, hydrochloride LC/MS (m/z) 445.1 (MH$^+$); RT=2.50; purity (UV, ELSD): 88%, 72%; yield: 20 mg.

1l {4-[5-Chloro-2-(3-methoxy-phenylsulanyl)-phenyl]-2(R)-methyl-piperazin-]-yl}-acetic acid, hydrochloride $^1$H NMR (DMSO-d6, 500 MHz) 1.32 (d, 3H), 3.05 (m, 1H) 3.10–3.40 (m, 4H), 3.50–3.60 (m, 2H), 4.10 (d, 1H), 4.24 (d, 1H), 6.82 (d, 1H), 6.95 (m, 3H), 7.11 (dd, 1H), 7.2 (s, 1H), 7.38 (dd, 1H)

LC/MS (m/z) 407.2 (MH$^+$); RT=2.41; purity (UV, ELSD): 99.6%, 100. %; yield: 1.26 g

1m {4-[2-(Biphenyl-4-yloxy)-phenyl]-2-methyl-piperazin-1-yl}-acetic acid, hydrochloride $^1$H NMR (DMSO-d6, 500 MHz) 7.60 (m, 4H); 7.40 (m, 2H), 7.32 (m, 1H), 6.95–7.20 (m, 6H), 5.00–6.50 (br, 1H), 4.00–4.10 (m, 1H), 3.80–3.90 (m, 1H), 3.20–3.50 (m, 6H), 3.05–3.15 (m, 1H), 1.17 (m, 3H);

LC/MS (m/z) 403.0; RT=2.45; purity: (UV/ELSD): 96.7%, 99.4; yield: 0.116 g (43%).

Example 2

2a (+/−)-{4-[2-(4-Methyl-phenylsulfanyl)-phenyl]-trans-2,5-dimethyl-piperazin-1-yl}-acetic acid, hydrochloride A solution of [2-(4-Methyl-phenylsulfanyl)-phenyl]-trans-2,5-dimethyl-piperazine (10 mg, 0.03 mmol) and diisopropylethylamine (0.02 mL, 0.11 mmol) was added to 4-[Chloroacetoxymethyl]phenoxymethyl polystyrene (100 mg, 0.09 mmol). The reaction mixture was agitated by shaking overnight at 70° C. The resin was filtered off and washed with N,N-dimethylformamide (4 mL), methanol (4 mL) and dichloromethane (4 mL). The resin was suspended in a 1:1 mixture of trifluoroacetic acid and dichlormethane (1.5 mL) and shaken at room temperature for 1 h. The resin was filtered off and washed with dichloromethane (1 mL). The organic extracts were collected and evaporated in vacuo. The crude product was purified by preparative LC-MS.

LC/MS (m/z) 371.1 (MH$^+$); RT=2.24; purity (UV, ELSD): 100%, 100%; yield: 1.6 mg.

The following compounds were prepared in an analogous fashion:

2b (+/−)-{4-[2-(4-iso-Propyl-phenylsulfanyl)-phenyl]-trans-2,5-dimethyl-piperazin-1-yl}-acetic acid, hydrochloride LC/MS (m/z) 399.0 (MH$^+$); RT=2.48; purity (UV, ELSD): 98.3%, 100%; yield: 2.2 mg.

2c (+/−)-{4-[2-(2,4-Dimethyl-phenylsulfanyl)-phenyl]-trans-2,5-dimethyl-piperazin-1-yl}-acetic acid, hydrochloride LC/MS (m/z) 385.0 (MH$^+$); RT=2.37; purity (UV, ELSD): 99.8%, 100%; yield: 4.7 mg.

2d (+/−)-2-{4-[2-(4-tert-Butyl-phenylsulfanyl)-phenyl]-3-methylpiperazin-1-yl}-propionic acid, hydrochloride LC/MS (m/z) 386.7 (MH$^+$); RT=2.14; purity (UV, ELSD): 91.9%, 99.2%; yield: 3.2 mg.

2e (+/−)-{4-[2-(4-Isopropyl-phenylsulfanyl)-phenyl]-piperazin-1-yl}-acetic acid, hydrochloride LC/MS (m/z) 370.8 (MH$^+$); RT=2.35; purity (UV, ELSD): 89.0. %, 99.9%; yield: 3.2 mg.

2f (+/−)-2-{4-[2-(4-Methoxy-phenylsulfanyl)-phenyl]-3-methyl-piperazin-1-yl}-propionic acid, hydrochloride LC/MS (m/z) 386.7 (MH$^+$); RT=2.63; purity (UV, ELSD): 91.9%, 99.2%; yield: 3.2 mg.

Pharmacological Testing

The compounds of the invention were tested in a well-recognised and reliable test measuring glycine uptake:

[$^3$H]-Glycine Uptake

Cells transfected with the human GlyT-1b were seeded in 96 well plates. Prior to the experiment the cells were washed twice in HBS (10 mM Hepes-tris (pH 7,4), 2,5 mM KCl, 1 mM CaCl$_2$, 2,5 mM MgSO$_4$,) and pre-incubated with test compound for 6 minutes. Afterwards, 10 nM $^3$H-glycine was added to each well and the incubation was continued for 15 minutes. The cells were washed twice in HBS. Scintillation fluid was added and the Plates were counted on a Trilux (Wallac) scintillation counter.

The test results showed, that the compounds of the invention all showed inhibition below 2000 nM as IC$_{50}$ in the above-mentioned assay. Most of the compounds were between 150 nM and 850 nM.

Microdialysis experiments in rodents showed that administration of selected compounds of the invention resulted in an increased concentration of glycine in the brain. Furthermore, in a rodent model of psychosis, selected compounds of the invention reversed the symptoms of amphetamine induced hyperactivity.

The invention claimed is:

1. A compound represented by the general formula I

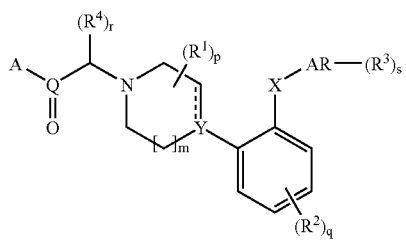

wherein
Y is N;
X represent O or S;
m is 1;
p is 0, 1, 2, 3 or 4;
q is 0, 1 or 2;
s is 0, 1, 2 or 3;
r is 0, 1 or 2;
Q represents C, P—OR$^5$, or S=O, wherein R$^5$ hydrogen or C$_{1-6}$-alkyl;
A is OR$^6$, wherein R$^6$ represent hydrogen, C$_{1-6}$-alkyl, aryl or aryl-C$_{1-6}$-alkyl, wherein aryl may be substituted with halogen, CF$_3$, OCF$_3$, CN, NO$_2$ or C$_{1-6}$ alkyl;
AR represents phenyl;
each R$^4$ individually represents C$_{1-6}$-alkyl, C$_{3-8}$-cycloalkyl or C$_{3-8}$-cycloalkyl-C$_{1-6}$-alkyl;
each R$^1$ is independently selected from the group consisting of C$_{1-6}$-alkyl, or two R$^1$ attached to the same carbon atom may form a 3–6-membered spiro-attached cycloalkyl;
each R$^2$ is independently selected from the groups consisting of halogen, cyano, nitro, C$_{1-6}$-alk(en/yn)yl, C$_{1-6}$-alk(en/yn)yloxy, C$_{1-6}$-alk(en/yn)ylsulfanyl, hydroxy, hydroxy-C$_{1-6}$-alk(en/yn)yl, halo-C$_{1-6}$-alk(en/yn)yl, halo-C$_{1-6}$-alk(en/yn)yloxy, C$_{3-8}$-cycloalk(en)yl, C$_{3-8}$-cycloalk(en)yl-C$_{1-6}$-alk(en/yn)yl, acyl, C$_{1-6}$-alk(en/yn)yloxycarbonyl, C$_{1-6}$-alk(en/yn)ylsulfonyl or —NR$^9$R$^{10}$ wherein R$^9$ and R$^{10}$ independently represent hydrogen, C$_{1-6}$-alk(en/yn)yl, C$_{3-8}$-cycloalk(en)yl, C$_{3-8}$-cycloalk(en)yl-C$_{1-6}$ alk(en/yn)yl or aryl, or R$^9$ and R$^{10}$ together with the nitrogen atom to which they are attached form a 3–7-membered ring which optionally contains one further heteroatom selected from the group consisting of nitrogen and oxygen;
each R$^3$ which is substituted on AR, is independently selected from the group consisting of halogen, cyano, nitro, C$_{1-6}$-alk(en/yn)yl, C$_{1-6}$-alk(en/yn)yloxy, C$_{1-6}$-alk(en/yn)ylsulfanyl, hydroxy, hydroxy-C$_{1-6}$-alk(en/yn)yl, halo-C$_{1-6}$-alk(en/yn)yl, halo-C$_{1-6}$-alk(en/yn)yloxy, C$_{3-8}$-cycloalk(en)yl, C$_{3-8}$-cycloalk(en)yl-C$_{1-6}$-alk(en/yn)yl, C$_{1-6}$-alk(en/yn)ylsulfonyl, aryl, aryl-C$_{1-6}$-alk(en/yn)yloxy, aryl-C$_{1-6}$-alk(en/yn)yl, C$_{1-6}$-alk(en/yn)yloxycarbonyl, acyl, —NHCO—C$_{1-6}$-alk(en/yn)yl, —CONR$^{11}$R$^{12}$ wherein R$^{11}$ and R$^{12}$ independently represent hydrogen, C$_{1-6}$-alk(en/yn)yl, C$_{3-8}$-cycloalk(en)yl, C$_{3-8}$-cycloalk(en)yl-C$_{1-6}$-alk(en/yn)yl or aryl, or R$^{11}$ and R$^{12}$ together with the nitrogen to which they are attached form a 3–7-membered ring which optionally contains one further heteroatom selected from the group consisting of nitrogen and oxygen;
or NR$^{13}$R$^{14}$ wherein R$^{13}$ and R$^{14}$ independently represent hydrogen, C$_{1-6}$-alk(en/yn)yl, C$_{3-8}$-cycloalk(en)yl, C$_{3-8}$-cycloalk(en)yl-C$_{1-6}$-alk(en/yn)yl or aryl; or R$^{13}$ and R$^{14}$ together with the nitrogen to which they are attached form a 3–7-membered ring which optionally contains one further heteroatom selected from the group consisting of nitrogen and oxygen;
or an acid addition salt thereof.

2. The compound according to claim 1 wherein X is S.
3. The compound according to claim 1 wherein Q is C.
4. The compound according to claim 1 wherein A is OH.
5. The compound according to claim 1 wherein p is 1 or 2.
6. The compound according to claim 1 wherein q is 0.
7. The compound according to claim 1 wherein r is 0 or 1.
8. The compound according to claim 1 wherein s is 1 or 2.
9. The compound according to claim 1 wherein AR is phenyl, r and q are both 0, p is 1 or 2, s is 1 or 2, r is 0 or 1, m is 1, R$^1$ is CH$_3$, A is OH, Q is C, Y is N and X is S.
10. The compound according to claim 9 wherein each R$^3$ is independently selected from the group consisting of halogen, C$_{1-6}$-alkoxy and C$_{1-6}$-alkyl.

11. The compound according to claim 10 wherein $R^3$ is selected from the group consisting of Cl, F, OCH$_3$, t-butyl, 2-propyl and methyl.

12. The compound according to claim 1 wherein $R^4$ is CH$_3$.

13. The compound according to claim 1, wherein said compound is selected from the group consisting of (+/−)-{4-[2-(4-Methoxy-phenylsulfanyl)-phenyl]-trans-2,5-dimethyl-piperazin-1-yl}-acetic acid (+/−)-{4-[2-(4-Chloro-phenylsulfanyl)-phenyl]-trans-2,5-dimethyl-piperazin-1-yl}-acetic acid (+/−)-{4-[2-(4-tert-Butyl-phenylsulfanyl)-phenyl]-trans-2,5-dimethyl-piperazin-1-yl}-acetic acid (+/−)-{4-[2-(4-Fluoro-phenylsulfanyl)-phenyl]-trans-2,5-dimethyl-piperazin-1-yl}-acetic acid (+/−)-{4-[2-(4-tert-Butyl-phenylsulfanyl)-phenyl]-2-methyl-piperazin-1-yl}-acetic acid (+/−)-{4-[2-(4-iso-Propyl-phenylsulfanyl)-phenyl]-2-methyl-piperazin-1-yl}-acetic acid (+/−)-2-{4-[2-(4-tert-Butyl-phenylsulfanyl)-phenyl]-trans-2,5-dimethylpiperazin-1-yl}-propionic acid {4-[5-Chloro-2-(4-methoxy-phenylsulfanyl)-phenyl]-2(R)-methyl-piperazin-1-yl}-acetic acid {4-[2-(4-Methoxy-phenylsulfanyl)-phenyl]-2(R),5(S)-dimethyl-piperazin-1-yl}-acetic acid {4-[5-Chloro-2-(4-methoxy-phenylsulfanyl)-phenyl]-2,2-dimethyl-piperazin-1-yl}-acetic acid (+/−)-{4-[5-Chloro-2-(4-trifluoromethyl-phenylsulfanyl)-phenyl]-2-methyl-piperazin-1-yl}-acetic acid {4-[5-Chloro-2-(3-methoxy-phenylsulfanyl)-phenyl]-2(R)-methyl-piperazin-1-yl}-acetic acid (+/−)-{4-[2-(4-Phenyl-phenyloxy)-phenyl]-2-methyl-piperazin-1-yl}-acetic acid (+/−)-{4-[2-(4-Methyl-phenylsulfanyl)-phenyl]-trans-2,5-dimethyl-piperazin-1-yl}-acetic acid (+/−)-{4-[2-(4-iso-Propyl-phenylsulfanyl)-phenyl]-trans-2,5-dimethyl-piperazin-1-yl}-acetic acid (+/−)-{4-[2-(2,4-Dimethyl-phenylsulfanyl)-phenyl]-trans-2,5-dimethyl-piperazin-1-yl}-acetic acid (+/−)-2-{4-[2-(4-tert-Butyl-phenylsulfanyl)-phenyl]-3-methylpiperazin-1-yl}-propionic acid {4-[2-(4-Isopropyl-phenylsulfanyl)-phenyl]-piperazin-1-yl}-acetic acid and (+/−)-2-{4-[2-(4-Methoxy-phenylsulfanyl)-phenyl]-3-methyl-piperazin-1-yl}-propionic acid, or a pharmaceutically acceptable acid addition salt of any of the foregoing compounds.

14. A pharmaceutical composition comprising a compound according to claim 1 or a pharmaceutically acceptable acid addition salt thereof and at least one pharmaceutically acceptable carrier or diluent.

15. A method for the treatment of psychoses, comprising administering to an animal body a therapeutically effective amount of a compound according to claim 1 or a pharmaceutically acceptable acid addition salt thereof to treat said psychoses.

16. The method of claim 15 wherein said animal body is a human body.

17. The method of claim 15 wherein said method is for the treatment of schizophrenia.

18. The method of claim 17 wherein said method is for the treatment of positive symptoms of schizophrenia.

19. The method of claim 17 wherein said method is for the treatment of negative symptoms of schizophrenia.

20. The method of claim 17 wherein said method is for the treatment of the positive and negative symptoms of schizophrenia.

21. A method for the treatment of convulsive disorders, comprising administering to an animal body a therapeutically effective amount of a compound according to claim 1 or a pharmaceutically acceptable acid salt thereof to treat said convulsive disorder.

22. The method of claim 21 wherein said animal body is a human body.

23. The method of claim 21 wherein said convulsive disorder is selected from the group consisting of epilepsy, spasticity, and myoclonus.

* * * * *